United States Patent [19]

Planck et al.

[11] Patent Number: 4,474,630
[45] Date of Patent: Oct. 2, 1984

[54] METHOD FOR THE PRODUCTION OF SYNTHETIC BLOOD VESSEL PROSTHESES

[75] Inventors: Heinrich Planck, Rottenberg; Peter Ehrler, Reutlingen, both of Fed. Rep. of Germany

[73] Assignee: Intermedicat GmbH, Emmenbrucke, Switzerland

[21] Appl. No.: 435,147

[22] Filed: Oct. 18, 1982

Related U.S. Application Data

[60] Continuation of Ser. No. 336,111, Dec. 30, 1981, abandoned, which is a continuation of Ser. No. 127,157, Mar. 4, 1980, abandoned, which is a division of Ser. No. 11,574, Feb. 12, 1979, abandoned.

[30] Foreign Application Priority Data

Feb. 14, 1978 [DE]  Fed. Rep. of Germany ....... 2806030

[51] Int. Cl.³ .............................. A61F 1/00; B32B 1/08
[52] U.S. Cl. ........................................ 156/62.4; 3/1.4; 156/175; 264/12
[58] Field of Search ...................... 156/167, 62.4, 172, 156/175, 246, 62.6; 3/1.4, 1; 264/5, 14, 8, 10, 6, 12, 13, 14; 428/308, 36, 403

[56] References Cited

U.S. PATENT DOCUMENTS

| 3,490,975 | 1/1970 | Lightwood et al. | 156/167 |
| 3,862,452 | 1/1975 | Wichterle et al. | 3/1.4 |
| 4,044,404 | 8/1977 | Martin et al. | 3/1.4 |

Primary Examiner—Michael Ball
Attorney, Agent, or Firm—Edwin E. Greigg

[57] ABSTRACT

A blood vessel prosthesis and a method of producing such a prosthesis in which single fibers having a sticky surface are sprayed onto a rod to form a tube from which the rod is subsequently removed, the fibers being formed in at least one layer, the fibers being applied to the rod in one or more selected directions and, in one form, the fibers, when stuck together, form a tube into which connective tissue cannot grow, the prosthesis having properties such as radial elastic expansibility, non-kinking and the like adaptable to those of natural arteries and views the tube may also be provided with an inner layer of flexible foil for impermeability or an outer coating to provide a smooth outer surface.

11 Claims, 4 Drawing Figures

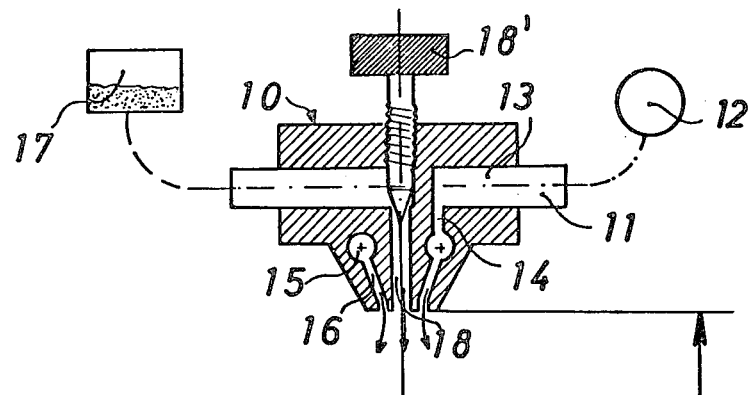
FIG. 1
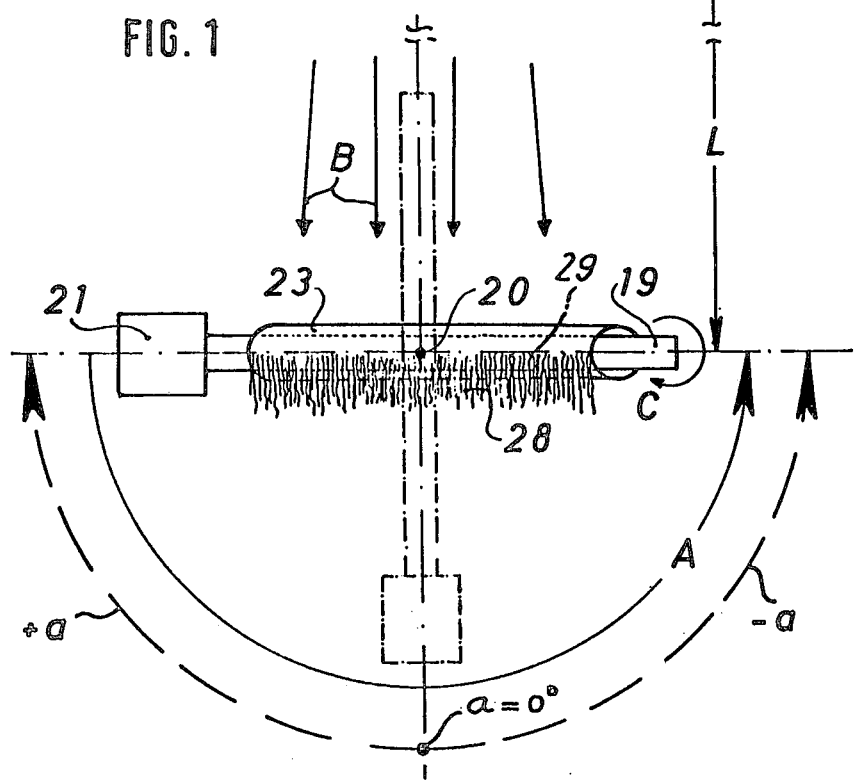

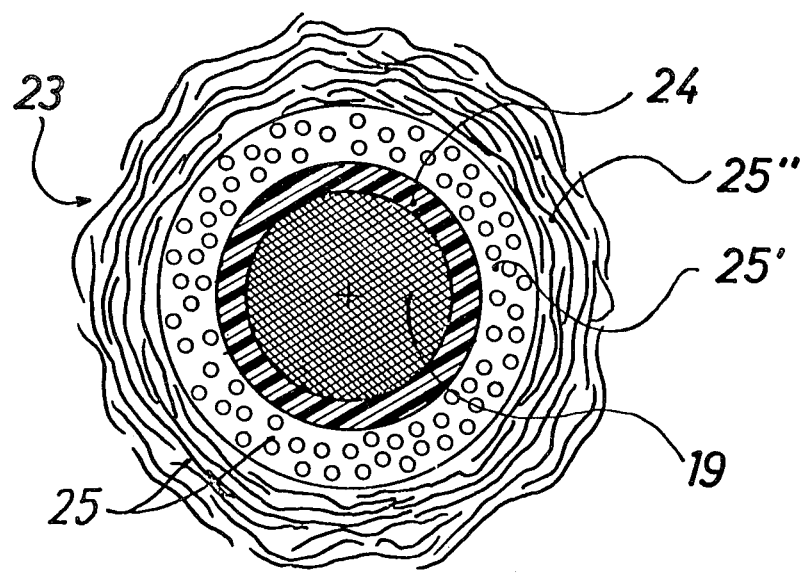

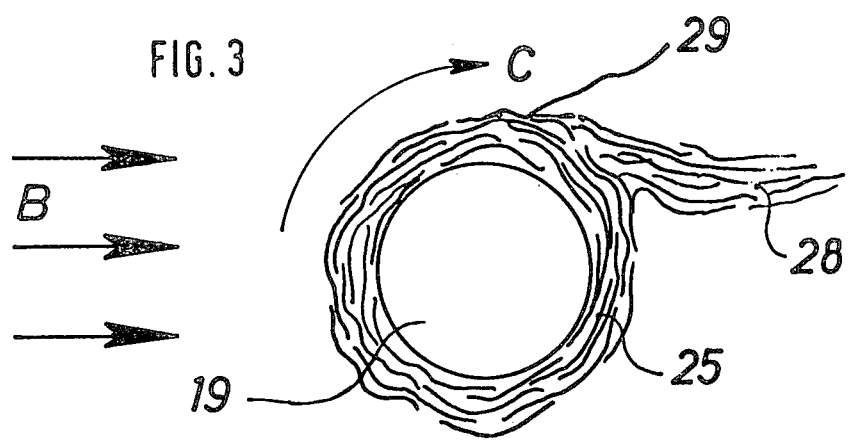
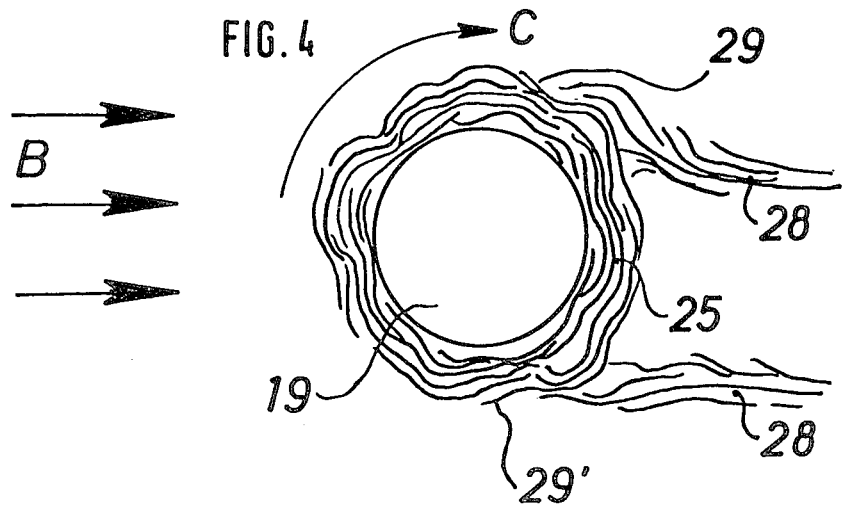

METHOD FOR THE PRODUCTION OF SYNTHETIC BLOOD VESSEL PROSTHESES

The is a continuation, of application Ser. No. 336,111 filed Dec. 30, 1981, now abandoned which is a continuation of Ser. No. 127,157 filed Mar. 4, 1980, now abandoned, which is a division of Ser. No. 11,574 filed Feb. 12, 1979, now abandoned.

BACKGROUND OF THE INVENTION

The invention relates to a method for the production of synthetic blood vessel prostheses and a synthetic blood vessel prosthesis produced by the method of the invention.

Blood vessel prostheses are tubes or pipes which are inserted as synthetic sections of arteries and veins in the medical practice for both human and animal medicine. Thus, blood vessel prostheses serve surgical purposes.

Synthetic blood vessel prostheses are known which are manufactured as seamless, accordion-pleated, knitted or woven tubes of yarn. The pleating of these tubes is intended to prevent kinking under heavy bending stress. Should they kink, the passage of blood through them would be greatly throttled or even entirely blocked. Such pleating, however, may disappear after implantation, either in the course of growing in or subsequently as well, to such an extent that the danger of kinking arises. Furthermore, the pleating causes turbulences in the flowing blood, which can be very disadvantageous. Also, the yarn forming the weave or knitting may be damaged by pleating, which results in weakened blood vessel prostheses. These blood vessel prostheses have the further property, which is often disadvantageous, that they are always substantially inelastic radially, or become inelastic in the course of time as a result of unavoidable ingrowth of connective tissue, the former being the case with woven blood vessel prostheses from the outset and the latter applying to knitted blood vessel prostheses. This is a property which natural blood vessels do not have, since natural blood-vessels expand when the blood pressure rises and retract in an elastic manner when the blood pressure goes down.

Knitted blood vessel prostheses also have the further disadvantage that at the connection point with the adjacent natural blood vessel (either artery or vein), the seam which forms this connection of the blood vessel prosthesis with the natural blood vessel can lead to raveling of the synthetic knitted blood vessel prosthesis.

Synthetic blood vessel prostheses are also formed as microporous, radially inelastic and thus not elastically expansible, bendable tubes of polytetrafluorethylene (PTFE). These tubes do avoid the danger of kinking; however, the lack of radial expansibility is often disadvantageous. Also, the material of these tubes creeps and as a result they stretch irreversibly over a relatively long period of time; this causes the physiological flow relationships of the blood in such tubes to change, which is disadvantageous and undesirable.

OBJECT AND SUMMARY OF THE INVENTION

It is one object of the invention to create a synthetic blood vessel prosthesis which can be bent to relatively small bend radii without the danger of kinking. It is also a purpose of the invention to make it possible, if desired, to produce blood vessel prostheses which are not only radially elastically expansible at the outset but also maintain this radial elastic expansibility for years after implantation and, if necessary, for many years, so that such a blood vessel prosthesis reversibly expands and retracts by the fluctuating or pulsating blood pressure, which is a property also held by natural arteries and veins.

It is also an objective of the invention to create a synthetic blood vessel prosthesis whose elastic properties are adaptable to those of natural arteries and veins, which is not the case with the known synthetic blood vessels referred to above.

In accordance with the invention, a method is provided for the production of synthetic blood vessel prostheses of polymeric synthetic material.

The tube formed in accordance with this method is formed from single fibers glued together, which one may also call a jacket, has excellent elastic properties, which can be very well approximated to those of natural arteries and veins. Thus, this tube is elastically bendable so that relatively small bend radii may be attained without the occurrence of the danger of kinking. As an example, there was a medical requirement for a straight, cylindrical blood vessel prosthesis with an inner diameter of 4 mm, such that it could be be bent with a bend radius of 20 mm without kinking. A first experimental attempt produced a straight prosthesis having a permissible bend radius of only 15 mm. Also, the method according to the invention easily permits the production of blood vessel prostheses which are radially elastically expansible in the manner of natural arteries and veins.

Should this radially elastic expansibility be intended to be maintained for years after the implantation in a body, this may be accomplished by forming a tube of single fibers glued together with one another, in such a manner that connective tissue cannot grow deeply into the tube after implantation. It does not harm the radial expansibility if connective tissue from the body only grows superficially into the tube for a short distance, or only superficially grows onto the tube thus connecting the tube with itself. This may be accomplished by producing a tube formed of single fibers glued together in such a manner that its cavities are sealed. If the tube formed of single fibers glued together is porous, then the tube is wrapped with a synthetic or other suitable foil which is wrapped with a synthetic or other suitable foil which is impermeable to connective tissue. The wrapping may be formed for example, by a dipping method, wherein the tube is introduced into a polymer solution while being rotated. This method forms a synthetic foil impermeable to connective tissue on the circumference of the tube.

In general, it is particularly favorable to assure lasting radial expansibility after implantation to produce the tube made up of single fibers in such a manner that its hollow spaces are sealed. This may be accomplished by the use of fibers of very low denier, which attach themselves to the rod while there is still a relatively low viscosity of its sticky surface layer, so that during the winding of these fibers on the rod to form the tube, the sticky surface layers coalesce, leaving hollow spaces formed by the fibers' crossing each other, in such a manner that no pores are created that penetrate the tube jacket; instead, hollow spaces into which the connective tissue cannot grow are formed.

If, in contrast, fibers are used which have a higher denier or which have only a very thin sticky surface layer when applied to the rod, which no longer has the tendency to coalesce, tubes made up of single fibers are produced which are porous or are even highly porous. In this case, connective tissue grows into the tube, completely penetrating its wall, and as a result this tube, as an implant, loses its radially elastic expansibility in the course of time. In some cases this is desirable, so that as a result of the method according to the invention, blood vessel prostheses can be produced which, depending upon what is desired, either retain their elastic expansibility or lose the original elastic expansibility as an implant.

Furthermore, as a result of selecting fibers having varying elasticity and other properties, by applying the fibers in one or more preferred directions with respect to the tube, by the rotational speed of the rod or the setting of the air circulation about the rod, of the staple diagram of the fibers employed, and so forth, one is substantially able to obtain the desired radial elasticity, bendability, freedom from kinking, and other properties in the tube being formed with single fibers.

The outer surface of the blood vessel prosthesis may usually advantageously be left in the rough form which occurs when manufactured from single fibers, since at least, in many cases, this corresponds to a desirable characteristic in the surface layer of the synthetic blood vessel prosthesis which provides a secure, rapid growth of connective tissue on the blood vessel prosthesis after its implantation, and this fixes the position of this prosthesis which forms a section of an artery or vein. However, cases can also be attained without difficulty, as needed, by means of suitable subsequent preparation, such as by applying a smooth coating of polymeric synthetic material.

In the same manner, the interior surface of the blood vessel prosthesis of the invention may be left in the rough state occasioned by the use of single fibers, or it may be given a different suitable property, which can be accomplished in various ways. In one preferred embodiment, when producing the prosthesis, the single fibers are applied to a seamless tube of flexible foil, preferably elastic synthetic foil, located on the rod; this foil tube then forms an inner tube of the finished blood vessel prosthesis and, since it is made of foil, it can easily form a perfectly smooth interior surface on the prosthesis as needed. This inner foil tube, which is produced in accordance with the method of the invention, may also be applied to the rod as a finished tube and can also be impermeable to fluids, or may be permeable only to certain blood components (enzymes, for example), and not to others. It can also be impermeable to connective tissue and thus can prevent the ingrowth of connective tissue through the wall of the prosthesis into its lumen.

If the prosthesis is so embodied that no connective tissue can grow into the lumen from the outside, this also permits the use of blood vessel prostheses having lumens of smaller diameter than was previously permissible. In fact, synthetic blood vessel prostheses used up to now were always porous, so that connective tissue could always grow into the lumen and constrict it; thus, for safety reasons, the diameter of the lumen could not be too small. This does not preclude the production of a blood vessel prosthesis in accordance with the invention such that, as already noted, it is porous and connective tissue can also grow into its lumen.

In addition, the force required to penetrate the prosthesis of the invention with surgical needles in order to sew it to natural blood vessels is less than in the known prostheses described above.

The blood vessel prosthesis according to the invention may take various forms. It may be cylindrical or circularly cylindrical, or it may be non-cylindrical. Its cross-sections may be round, oval, elliptical or the like. Its diameter and/or its cross-sectional form can also be varied over its length, either continuously, in steps, or the like.

The production of the single fibers maybe accomplished in various ways. In a preferred and very particularly advantageous form of a method according to the invention, all the fibers, or at least a substantial part of the fibers, are created by means of fiber spraying; that is, a polymeric solution is sprayed under pressure out of a spray or atomizer nozzle, whereby fibers are then formed of this solution as soon as it exits into the air, these fibers having varying lengths and thicknesses. These fibers then are transported to the rod, either as a result of the spray pressure itself or by means of a supplementary air current, which may preferably be provided by means of compressed air which flows together with the polymeric solution out of the same nozzle aperture. During this procedure, depending upon the air guidance, not all the fibers reach the rod. The lost fibers can be redissolved and the solution can be used again.

In general, it is particularly advantageous when all the single fibers of the particular blood vessel prosthesis are created by means of fiber spraying. This in fact produces fibers which, immediately after they are produced, have a sticky surface, which can easily remain sticky until such time as they have been wound on the rod. If it is provided instead, which can also be possible and efficient in many cases, that the single fibers are obtained by dissolving a fiber band, such as a fiber band produced on a drawing frame, and are then transported pneumatically to the rod, then during their flight to the rod, these fibers must be sprayed with solvents or bonding agents so that their surface will become sticky, unless these fibers are used as a supplement to fibers produced by fiber spraying and are also made sticky by the sticky fibers produced by fiber spraying.

Single fibers made of polyurethane have proven to be very particularly advantageous. Their elasticity produces blood vessel prostheses which have particularly favorable radial elastic properties, as demonstrated in experiments. However, other fibers of polymeric synthetic materials can also be used, should this from case to case be efficient; thermoplastic synthetic materials are preferable.

Winding the single fibers on the rod to form the tube or jacket may take place preferably solely by rotating the rod. However, it is also conceivable that this winding may be effected by an air current circulating about the rod, which preferably may have an axial component extending in the axial direction of the rod; that is, it can circulate about the rod in a pattern of spiral or helical lines. If necessary, such a circulating air current can also be combined with a rotation of the rod. It is also conceivable that when fibers produced by spraying are used, the spray or atomizer nozzle which sprays the polymeric solution rotates about the rod.

It is further conceivable that the single fibers be permitted to travel onto the circumference of the rod (that is, of the tube then being formed) directly from a feed roller pair which transports them, without intermediate pneumatic transport means, and that they be sprayed at the windup line, or prior thereto, with glue or with a solvent which makes their surface sticky.

In many cases, it is sufficient to use only one type of single fibers having the same staple characteristics, but the invention also contemplates the use of single fibers having different staple characteristics, if desired.

The invention also encompasses blood vessel prostheses produced in accordance with the method of the invention wherein the single fibers forming a tube are oriented in a specific direction.

The invention will be better understood as well as further objects and advantages thereof become more apparent from the ensuing detailed description of preferred embodiments taken in conjunction with the drawings.

BRIEF DESCRIPTION OF THE DRAWINGS

FIG. 1 is a schematic perspective view of one embodiment of an apparatus by means of which blood vessel prostheses in accordance with the invention may be produced;

FIG. 2 is an enlarged, substantially schematic, cross-sectional view through a blood vessel prosthesis according to the invention;

FIG. 3 is an enlarged, substantially schematic, cross-sectional view through a blood vessel prosthesis according to the invention at one stage of manufacture, and showing the embodiment of one fiber beard; and FIG. 4 is an enlarged, substantially schematic, cross-sectional view through a blood vessel prosthesis according to the invention at one stage of manufacture, and showing the embodiment of two fiber beards.

DESCRIPTION OF THE PREFERRED EMBODIMENTS

In FIG. 1, there is shown a pneumatic atomizer nozzle 10 which has an attachment nozzle 11 for compressed air supplied by a compressed air source 12. The compressed air flows out through a channel 13 and cross channels 14 into an annular chamber 15 and from there through an annular gap 16 encompassing a cannula 18 and thereby sprays polymeric solution flowing out of the cannula 18 for the purpose of forming single fibers. This polymeric solution may be aspirated by means of the underpressure generated by the compressed air, and/or may flow out of the cannula 18 by means of an underpressure generated in the interior of the supply reservoir 17 containing the polymeric solution. The supply reservoir 17 may thus be either under interior overpressure or not, depending upon what is desired. The required quantity of polymeric solution is also adjustable by means of an adjustment needle 18'.

The polymeric solution is preferably a liquid polyurethane solution; however, other suitable solutions of polymeric synthetic materials which produce single fibers after they escape from the cannula 18 can also be considered; this method of producing the fibers may be designated as fiber atomization. The polymeric solution is sprayed as a result of the compressed air, so that the polymeric synthetic fibers form in the air downstream of the atomizer nozzle 10; for a short time, these fibers have a sticky surface layer, whose viscosity is adjustable by means of the solvent component percentage of the polymeric solution.

A rod 19 is disposed at a distance L from the nozzle 10, the longitudinal axis of which always crosses the central longitudinal axis of the nozzle 10 at the point 20 in an efficient manner; however, as needed, it may also pass the longitudinal axis of the nozzle 10 laterally. The rod may also be arranged differently relative to the atomizer nozzle, if needed, as is appropriate in some cases. It is particularly advantageous to adjust the position of the rod either discontinuously or continuously during the manufacture of a blood vessel prosthesis.

In the embodiment of FIG. 1, the rod 19 can be rotated by 180°, either by means of a motor or by hand, about the point 20 in the plane of the drawing, out of the fully extended position shown in the direction of the arrow A. This rod 19 is further rotatable about its longitudinal axis by means of a motor 21 having an adjustable speed. The speed may be, for example, 20 to 200 rpm, and depending upon requirements, it may be set to remain constant or may be varied during the manufacture of the prosthesis.

The rod 19 may be cylindrical, conical, or other shape, either rotationally symmetrical or not, depending upon the requirements imposed by the lumen of the synthetic blood vessel prosthesis 23 (artery or vein) which is to be formed on this rod.

The angular positions of the rod 19 measured outward at both sides from the position of the rod 19 shown in dot-dash lines in alignment with the longitudinal axis of the atomizer nozzle 10 are marked $+a$ and $-a$.

In order to produce a prosthesis 23 on the rod, angles $a$ between $+45°$ and $+90°$ and between $-45°$ and $-90°$ are generally involved. In duplicating the design of the walls of natural arteries and veins, whose fibrils cross each other in layers, it is particularly effective for the tube 25 made up of fibers to be provided with a layered design in which the fibers of adjacent layers cross each other. This can be easily accomplished by setting the rod 19 at a positive angle $\underline{a}$ while building up one fiber layer and at a negative angle $\underline{a}$ while building up the overlying fiber layer. For example, a fiber layer 25' (FIG. 2) may be formed on the rod 19 rotating about its longitudinal axis, where the angle $\underline{a} = +50°$, and subsequently to set the rod 19 at an angle $\underline{a} = +-60°$, at which angular setting a further fiber layer 25" is applied to the rod 19 while the rod 19 rotates about its longitudinal axis. The fiber layers 25' and 25" may be firmly connected to one another, or may be borne loosely one upon the other, depending upon the requirement placed on the blood vessel prosthesis.

In FIG. 2, which represents a cross section through a synthetic blood vessel prosthesis in the form of an artery or vein produced on the rod 19, this blood vessel prosthesis 23 comprises the inner foil tube 24 having a wall thickness of from 0.01 mm to 0.5 mm and an outer tube 25 made up of single fibers stuck together. The latter tube comprises the mutually coaxial layers 25' and 25", while the single fibers in each layer 25', 25" have a certain preferred direction, as noted above. These two preferred directions are different and may preferably intersect.

In FIG. 1, the distance between the nozzle 10 and the point 20 is marked as L.

The rod 19 may be made of metal or some other substance. Preferably, it may be of a synthetic material so that after the prosthesis 23 is produced it can be removed from the interior of the prosthesis 23 by being dissolved; by this means, all danger of damage to the prosthesis is avoided.

The production of a synthetic artery or vein 23 on the rod 19 in the embodiment of FIG. 1 will now be described in more detail.

In this advantageous embodiment, the single fibers being created downstream of the atomizer nozzle 10, which are still sticky, are blown toward the rod 19 solely by the compressed air flowing out of the annular gap 16, so that no other air is required for the transport of these fibers to the rod. Naturally, all the fibers do not reach the rod. The fibers which pass the rod 19 at the side may be collected and conveyed back to the solution.

In the illustrated method of manufacture, which is particularly advantageous, the following is also true: Fibers produced by the spraying method have different lengths and different deniers. Their fineness and their staple diagram may be varied by means of the pressure with which they excape from the cannula 18 or the underpressure generated by the compressed air, or by means of an overpressure generated in the interior of the supply reservoir 17 containing the polymeric solution, and furthermore by means of the type of polymeric solution and the quantity of the polymeric solution escaping from the cannula 18 over a period of time. The viscosity of the polymeric solution may always be variably set by means of variable percentage quantities of solvent, and also by this means both the sticky properties of the fibers and their length can be varied. The elasticity of the single fibers depends on the polymeric synthetic material used. As noted, polyurethane solutions can advantageously be provided as the polymeric solution.

The tube 25 made up of the single fibers (that is, the outer tube of the blood vessel prosthesis 23, if there is an inner foil tube 24, as is preferably the case; however, the inner foil tube 24 may also be omitted) may advantageously be produced by the apparatus illustrated in FIG. 1 in such a manner that the sticky single fibers created by fiber spraying, which are pneumatically transported to the rod 19 by means of the air current generated by the compressed air flowing out of the annular gap 16 of the nozzle 10, forms fiber beard 28 on at least one side of the exterior circumference of the synthetic fiber tube 25 then being produced.

The rotary speed of the rod 19 is selected to be such that the length of this fiber beard 28 adopts a stationary average value, which can preferably approximately correspond to the length of the longest single fibers. The newly arriving single fibers stick to the fiber beard 28 as a result of their sticky surface. The fiber beard 28 extends, from the atomizer nozzle 10 outward, toward one or both longitudinal sides of the rod 19 in a direction away from the atomizer nozzle 10 and is continually wound around the circumference of the rod 19 as a result of the rotation of the rod 19 about its longitudinal axis in a rotary direction C. The base of the fiber beard begins approximately at the jacket line 29 or 29' of the pertinent exterior circumference of the blood vessel prosthesis being produced at that time. Depending upon the requirements of the method, one fiber beard (FIG. 3) is formed on a jacket line 29, or two fiber beards 28 (FIG. 4) are formed on two approximately diametrically opposite jacket lines 29 and 29', which are approximately the jacket lines at which the air flow B breaks away from the particular tube circumference.

In FIG. 3 and FIG. 4, the rotary direction is marked C. The rotary speed of the rod 19, however, is selected to be such that, as noted, the fiber beard 28 is always present, so that the newly arriving single fibers reaching it become "stuck" to this fiber beard 28, lengthening its open end. At the same speed at which this fiber beard 28 is lengthened, the fiber beard is wound on the rod 19, so that a stationary length of the fiber beard 28 results. The newly arriving fibers are thus applied to the fiber beard similarly to the open-end spinning process, lengthening its open end. However, these single fibers are not twisted together into a yarn, but rather they are oriented in the direction of the air flow B as a result of the air flow, which at the rod 19 has the direction shown by the arrows B, generated by the compressed air flowing out of the atomizer nozzle 10; thus, they are wound on the rod 19 having this preferred direction.

If the angle $\underline{a}$ is then smaller that $+90°$ and $-90°$ and is larger than $0°$, a helical winding of fibers of the fiber beard 28 onto the rod 19 takes place. Depending upon their length, the fibers then extend about the rod 19 at an angle smaller than 360° or at an angle which either corresponds to or is greater than 360°. In the fiber atomization process, fibers can even be created which can only be wound about the rod less than 360°, as well as those which are wound about the rod more than 360°. The single fibers forming the fiber beard 28 are not oriented exactly parallel to one another, but rather they have only a preferred direction parallel to the air flow B. Depending upon the application of these single fibers onto the beard 28, isolated fibers can also extend partially transversely to the air flow B. In every case, however, one preferred direction of the fibers in the fiber beard 28, and thus in the tube 25 made up of single fibers, is set; this preferred direction, as noted, can be varied either continuously or discontinuously by varying the angle $\underline{a}$ between $+90°$ and $-90°$. It is generally particularly advantageous to form a plurality of layers 25' and 25'' (FIG. 2) which have intersecting preferred directions of their single fibers. Naturally, more than two such layers may be formed.

The apparatus illustrated in FIG. 1 thus enables extraordinarily broad variability of blood vessel prostheses to be produced, as was not possible earlier.

PRODUCTION EXAMPLES

Some special production examples are described below which were produced by means of the apparatus illustrated in FIG. 1 and which led to synthetic blood vessel prostheses which are outstandingly well suited for use in human medicine.

In the following production examples, the following physical dimensions were uniformly selected:

Distance L=1.5 m.

As the atomizer nozzle 10, a pneumatic atomizer sold by the Lechler company, Stuttgart, type number DRS 142, was used.

The compressed air pressure at the inlet of the atomizer nozzle 10 was 2.5 bar. There was a throughput of compressed air through the atomizer nozzle 10 of 16 N m³/h (free air flow rate expressed in cubic meters per hour). In the supply reservoir 17, a constant overpressure of 3 bars was always maintained, which was exerted on the polymeric solution located within it.

The rotary speed of the rod 19 about its longitudinal axis was between 20 and 50 rpm.

PRODUCTION EXAMPLE 1

A circular rod 19 of polyvinyl alcohol having an exterior diameter of 4 mm was used. On the rod, a synthetic blood vessel prosthesis was produced by means of spraying a polyurethane solution made up according to composition 1 (described hereinafter); thus, this prosthesis comprised only single fibers stuck to each other.

The quantity of polyruethane solution sprayed was 200 grams and duration of spraying was 17 minutes.

As the blood vessel prosthesis, a tube made up of two layers was produced, whereby during the production of the single layer, the rod 19 rotated constantly and was set at a particular angle $\underline{a}$ each time:
First layer:
  Angle $\underline{a} = +60°$
  Layer thickness: 0.45 mm
Second layer:
  Angle $\underline{a} = -60°$
  Layer thickness: 0.45 mm The wall thickness of the blood vessel prosthesis was 0.9 mm.

After drying on the rod 19 at 22° C. for five minutes, the blood vessel prosthesis was pushed off from the rod 19 and was hung up for further drying.

The inner surface of the blood vessel prosthesis thus produced was fibrously rough and the wall was porous. The outer surface was also fibrously rough.

PRODUCTION EXAMPLE 2

As the rod 19, a cylindrical tube of polyvinyl alcohol having an exterior diameter of 6 mm and a wall thickness of 1 mm was used, which was drawn over a circularly cylindrical steel rod having an exterior diameter of 4 mm.

Onto this rod 19, an inner foil tube was applied and the polymeric solution used for this was produced according to Composition 2 (described hereinafter). The thickness of the inner foil tube which was produced was 0.07 mm. For the fiber spraying, a polymeric solution according to Composition 3 (described hereinafter) was used.

The quantity of polymeric solution sprayed was 200 grams and the duration of spraying was 12 minutes. Again at brief intervals, while the rod 19 was rotated, two fiber layers were produced in which the fibers had different preferred directions.
First layer:
  Angle $\underline{a} = +45°$
  Layer thickness: 0.35 mm
  Quantity of polymeric solution used: 100 g
Second layer:
  Angle $\underline{a} = -45°$
  Layer thickness: 0.35 mm
  Quantity of polymeric solution used: 100 g The two layers had different fiber density; the first layer had the higher fiber density and the second layer the lower fiber density.

This was accomplished by means of a higher throughput over time of polymeric solution through the nozzle 10 (the adjustment was made by means of the needle 18' in FIG. 1) when producing the first layer 25', in comparison with that during the production of the second layer 25".

After the blood vessel prosthesis was dried for 15 minutes on the rod at room temperature (22° C.), the prosthesis could be pushed off the rod and was hung up for further drying. This synthetic blood vessel prothesis comprising the inner foil tube and the two-layered fiber outer tube firmly connected thereto had a smooth inner surface and a fibrously rough outer surface. The inner foil tube prevents the ingrowth of connective tissue. However, connective tissue can grow through the first layer to the second layer; as a result, this prosthesis is fixed in position in the body in which it is implanted.

PRODUCTION EXAMPLE 3

A rod 19 of steel was used, whose diameter was 4 mm. As an inner foil tube, a conventional commercial foil tube, produced in a seamless manner by the worm screw extrusion process, was used which was made of the same basic substance as was used for producing Composition 4 (described hereinafter). The wall thickness of the foil tube was 0.1 mm. The polymeric solution used for fiber spraying was made up according to Composition 4; the sprayed quantity was 275 g; and two fiber layers were produced having the same fiber density.
First layer:
  Angle $\underline{a} = +50°$
  Layer thickness: 0.5 mm
Second layer:
  Angle $\underline{a} = -50°$
  Layer thickness: 0.5 mm
  Duration of spraying: 12 minutes
  Total layer thickness: 1.1 mm The finished prosthesis was pushed off the rod 19 and hung to to dry at room temperature. The result was a synthetic blood vessel prosthesis having a very smooth inner surface. The outer surface was rough and not porous.

Composition Used:
Composition 1

This composition is an aromatic polyurethane in granulated form, produced by the B. F. Goodrich company, Holland, with the type designation ESTANE 5714 F1 Resin.

The properties of the polyurethane according to the manufacturer:
  Specific gravity: 1.11 g/cm$^3$
  Ultimate tensile strength: 3600 N/cm$^2$
  Breaking elongation: 560%
  Shore hardness A: 80°

10 parts of this granulate were dissolved in 14 parts of acetone and 10 parts of n,n-dimethylformamide.

Composition 2

The product used was an aliphatic polyesterurethane produced and sold by Bayer AG, Leverkusen, under the type designation "Impranil ELH", in solution form.

The properties of the material according to the manufacturer:
  Viscosity of the solution: 350 Poise (25° C.)
  Film properties:
  Hardness Shore A: 88°
  Ultimate tensile strength: 5200 N/cm$^2$
  Breaking elongation: 420%
  Supplied form (according to the manufacturer): Impranil ELH solution in xylol/isopropanol/ethylglycol = 29:20:21, ca. 30% solution 40 parts of this solution were diluted with 5 parts isopropanol, 40 parts toluol and 14 parts n,n-dimethylformamide.

Composition 3

The product used is identical to that of Composition 2: a 30% solution of an aliphatic polyesterurethane, produced by Bayer AG, Leverkusen. 200 parts of this solution were diluted with 25 parts acetone, 150 parts toluol and 20 parts isopropanol.

Composition 4

The basic substance is a polyetherurethane in granulated form, produced and sold by the Upjohn Company, USA, under the type designation "Pellethane CPR 2363-λA Urethane Elastoplastic Polymer".

Properties of this polyetherurethane according to the manufacturer:

Specific gravity: 1.13 g/cm$^3$
Ultimate tensile strength: 4200 N/cm$^2$
Breaking elongation: 550%

400 parts of this granulate were dissolved in 650 parts acetone, 70 parts isopropanol and 300 parts n,n-dimethylformamide.

Blood vessel prostheses produced according to the novel method of the invention may, if desired, be subsequently treated, for example, in order to make them hydrophilic or hydrophobic or negatively charged, depending upon the desired boundary surface properties of the prosthesis. The following treatments of the inner surface are preferably to be considered, either singly or in suitable combinations (these treatment methods are per se known in synthetic materials, so that they need not be explained in detail to one skilled in the art):

(a) Stuffing by the addition of a radical initiator into the polymer.

(b) Gamma irradiation of the surface, with a resultant chemical reaction in the polymer.

(c) Gamma irradiation of the surface in the presence of a monomer under the effect of a buffer gas.

(d) Embedding of different polymer particles into the polymer surface, which in turn already has the desired and necessary boundary surface properties with respect to the blood and its components and thus characterizes the thus-produced surface of the original polymer.

Other known methods are suitable as well for modifying the boundary surface properties of the inner surfaces of the synthetic blood vessel prostheses.

When a plurality of fiber layers, such as the fiber layers 25' and 25'', are produced, then the method may be selected to be such that adjacent layers are either stuck together or not. In the latter case, one layer encompasses the layer located within it only loosely; however, these layers are restricted in mutual axial displacement by the roughness of the adjacent layer surfaces. Making the adjacent layers stick together is simply accomplished when making the transition from one layer to the next layer by not permitting the outer surface of the just-produced layer to dry; that is, either fiber spraying is continued while the rod 19 is angularly adjusted or it is interrupted only briefly and the rod 19 is then placed in the new angular position, so that the surface of the first layer produced is still sticky when the first fibers intended for the next layer arrive. If instead, the fiber spraying is interrupted after the production of a layer until the outer surface of this layer is dry, and then fiber spraying only begins with the production of the next layer, so that there is no sticking connection between the two layers in the above-described embodiments, although the fibers of the second layer arrive at the first layer while sticky.

In FIG. 1, the illustrated apparatus has a single atomizer nozzle. Then, a tube forms on the rod from the fibers created by fiber spraying and suspended and wound thereon; the length of these fibers is approximately determined by the section of the rod 19 which lies within the conically shaped fiber-air flow generated by the atomizer nozzle 10. Naturally, it is generally efficient to further shorten the finished prosthesis at both ends. Should it be desirable to produce longer blood vessel prostheses than can be produced with a single atomizer nozzle 10 without axially adjusting the rod 19, one may arrange two or more atomizer nozzles at appropriate distances from each other, which together simultaneously produce a correspondingly longer prosthesis on a correspondingly longer rod 19.

The foregoing relates to preferred embodiments of the invention, it being understood that other embodiments and variants thereof are possible within the spirit and scope of the invention, the latter being defined by the appended claims.

What is claimed and desired to be secured by Letters Patent of the United States is:

1. A method for producing a tube-like synthetic blood vessel prosthesis on a support means comprising: directing a compressed air medium along and surrounding a nozzle, aspirating a solution of a polymer through said nozzle into said compressed air medium surrounding said nozzle to form individual polymer fibers, directing said compressed air toward said support means, forcing the formed polymer fibers by means of the compressed air medium onto said support means to form a fiber beard thereon, tilting said support means at a first angle relative to the direction in which the polymer fibers are forced and simultaneously rotating said support means about its longitudinal axis to wind the beard of polymer fibers on said support means on an angle relative to the longitudinal axis of the support means.

2. A method as set forth in claim 1 in which subsequent to winding the polymer fibers at the first tilt angle, tilting the support means at a second tilt angle to form fibers at a different angle relative to the longitudinal axis of the support means.

3. A method as set forth in claim 2 which comprises applying a layer of a sticky substance on said support means prior to forming said polymer fibers and prior to forcing the polymer fibers onto the support means.

4. A method as set forth in claim 3 in which said foil tube is coated with a layer of a sticky substance prior to forming said beard on said rod.

5. A method for producing a tubular blood vessel prosthesis by producing individual fibers of a polymer by passing a solution of a polymer through a nozzle into a surrounding gaseous medium, transporting these individual fibers to a rod and winding the individual fibers onto the rod, characterized in that the solution passes through the nozzle into a gaseous medium disposed in front of the nozzle to form individual fibers in the gaseous medium;

transporting the individual fibers to the rod by means of the gaseous medium to form a fiber beard on the rod with the beard being oriented in the downstream direction on the rod; and circulating an air current about the rod so that the air current has a component extending in the axial direction of the rod in order to wind the beard thereon in a spiral direction relative to the rod.

6. A method for producing a tube-like synthetic blood vessel prosthesis on a support means comprising: directing a gaseous medium along a nozzle axis, causing a polymeric solution to flow from said nozzle into said gaseous medium to produce individual linear fibers from said solution, directing said gaseous medium toward said support means thereby transporting the individual linear fibers to said support means by means of the gaseous medium to form a fiber beard on the support means with the beard being oriented in the downstream direction of the support means, and simultaneously rotating the support means about its longitudinal axis while the beard is being wound thereon, thereby causing said fibers to wind on said support means in a crossed relationship.

7. A method for producing a tube-like synthetic blood vessel prosthesis on a support means comprising:
directing a gaseous medium along a nozzle axis,
causing a polymeric solution to flow from said nozzle into said gaseous medium to produce individual linear fibers from said solution, directing said gaseous medium toward said support means thereby transporting the individual linear fibers to said support means by means of the gaseous medium to form a fiber beard on the support means with the beard having a preferred main fiber direction and divergent other fiber directions and being oriented in the downstream direction of the support means causing said fibers to wind on said support means in a crossed relationship.

8. A method for producing a tube-like synthetic blood vessel prosthesis on a support means comprising:
directing a gaseous medium along a nozzle axis,
causing a polymeric solution to flow from said nozzle into said gaseous medium to produce individual linear fibers from said solution, directing said gaseous medium toward said support means thereby transporting the individual fibers to said support means by means of the gaseous medium to form a fiber beard on said support means with the beard having a preferred main fiber direction and divergent other fiber directions and being oriented in the downstream direction of said support means and simultaneously rotating said support means about its longitudinal axis while the angular relationship of said support means and nozzle are changed relative to one another and the beard is wound on said support means in a crossed angular relationship.

9. A method as set forth in claim 8 in which a layer of a sticky substance is applied onto said support means prior to forming said polymer fibers and prior to forcing the polymer fibers onto the support means.

10. A method as set forth in claim 8 in which during rotation of the support means to wind the polymer fibers thereon the rod is tilted at a first angle, and subsequently tilting the rod at a second tilt angle to form fibers at a different angle relative to the longitudinal axis of the rod.

11. A method as set forth in claim 10 in which a layer of a sticky substance is applied onto said support means prior to forming said polymer fibers and prior to forcing the polymer fibers onto the support means.

* * * * *